United States Patent
Ham et al.

(10) Patent No.: US 10,653,732 B2
(45) Date of Patent: May 19, 2020

(54) COMPOSITION FOR STIMULATING INSULIN SECRETION FROM CELLS AND USE THEREOF

(71) Applicant: KOREA INSTITUTE OF SCIENCE AND TECHNOLOGY, Seoul (KR)

(72) Inventors: Jungyeob Ham, Gangneung-si (KR); Bong Chul Chung, Seoul (KR); Taejung Kim, Gangneung-si (KR); Pilju Choi, Gangneung-si (KR); Ki Sung Kang, Seongnam-si (KR); Buyng Su Hwang, Sangju-si (KR); Kyu Sun Kim, Gangneung-si (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 219 days.

(21) Appl. No.: 15/935,634

(22) Filed: Mar. 26, 2018

(65) Prior Publication Data

US 2018/0280456 A1    Oct. 4, 2018

(30) Foreign Application Priority Data

Mar. 27, 2017   (KR) .................. 10-2017-0038710

(51) Int. Cl.
| | | |
|---|---|---|
| *A61K 36/062* | (2006.01) | |
| *A61P 3/10* | (2006.01) | |
| *A61K 31/122* | (2006.01) | |
| *A23L 33/10* | (2016.01) | |
| *A61K 31/05* | (2006.01) | |
| *C07C 35/44* | (2006.01) | |
| *C07C 39/205* | (2006.01) | |
| *C07C 39/14* | (2006.01) | |

(52) U.S. Cl.
CPC ............ *A61K 36/062* (2013.01); *A23L 33/10* (2016.08); *A61K 31/05* (2013.01); *A61K 31/122* (2013.01); *A61P 3/10* (2018.01); *A23V 2002/00* (2013.01); *A23V 2250/208* (2013.01); *A61K 2236/39* (2013.01)

(58) Field of Classification Search
None
See application file for complete search history.

(56) References Cited

FOREIGN PATENT DOCUMENTS

WO    WO 00/02839 A1    1/2000

OTHER PUBLICATIONS

U.S. Appl. No. 16/282,203, filed Feb. 2019, Ham, Jungyeob.*
Fukai et al., "Antiangiogenic Activity of Hypoxylonol C", Journal of Natural Products, vol. 77, 2014, pp. 1065-1068.
Fukai et al., "Hypoxylonols C-F, Benzo[j]fluoranthenes from Hypoxylon truncatum", Journal of Natural Products, vol. 75, 2012, pp. 22-25.
Korean Notice of Allowance for Korean Application No. 10-2017-0038710, dated Mar. 9, 2018.
Korean Office Action for Korean Application No. 10-2017-0038710, dated Dec. 13, 2017.
Koyama et al., "Hypoxylonols A and B, Novel Reduced Benzo[j]fluoranthene Derivatives from the Mushroom Hypoxylon truncatum", Journal of Natural Products, vol. 65, No. 10, 2002, pp. 1489-1490.
Sudarman et al., "Truncatones AeD, benzo[j]fluoranthenes from *Annulohypoxylon* species (*Xylariaceae, Ascomycota*)", Tetrahedron, vol. 72, 2016, pp. 6450-6454.

* cited by examiner

*Primary Examiner* — Michael Barker
(74) *Attorney, Agent, or Firm* — Birch, Stewart, Kolasch & Birch, LLP

(57) ABSTRACT

Provided are a composition for stimulating insulin secretion from cells, the composition including a *Hypoxylon truncatum* extract or an active ingredient thereof, and a method of stimulating insulin secretion from cells.

14 Claims, 6 Drawing Sheets

COMPOSITION FOR STIMULATING INSULIN SECRETION FROM CELLS AND USE THEREOF

CROSS-REFERENCE TO RELATED APPLICATION

This application claims the benefit of Korean Patent Application No. 10-2017-0038710, filed on Mar. 27, 2017, in the Korean Intellectual Property Office, the disclosure of which is incorporated herein in its entirety by reference.

BACKGROUND

1. Field

The present disclosure relates to a composition for stimulating insulin secretion from cells, and a method of stimulating insulin secretion from cells.

2. Description of the Related Art

Diabetes is a kind of systemic metabolic disorders caused by genetic or environmental factors and is a disease caused by absolute or relative insulin deficiency in the body. Major symptoms include abnormal hyperglycemia and urinary glucose due to abnormalities in carbohydrate, fat, and protein metabolisms, and are characterized by increased hunger, increased thirst, and needing to urinate, together with extreme fatigue and tiredness.

Diabetes is largely classified into insulin-dependent type 1 diabetes and insulin-independent type 2 diabetes. In the case of insulin-dependent type 1 diabetes, severe insulin deficiency leads to sudden onset of symptoms, and serious complications such as diabetic ketoacidosis are also found. Insulin-dependent type 1 diabetes mainly occurs in young people aged 10-20, and thus is also called juvenile diabetes. Type 2 diabetes develops mainly in people older than the age of 40, and accounts for most of diabetes patients in Korea. Unlike type 1 diabetes, type 2 diabetes is called adult onset diabetes, and the causes are not clarified yet. However, genetic and environmental factor are known to be involved in occurrence of type 2 diabetes. Genetic factors show diverse familial clustering and a concordance rate in identical twins reaches 90%-100%. If both parents have type 2 diabetes, offspring has 58% chance of developing diabetes. If one of both parents has type 2 diabetes, offspring has 27% chance of developing diabetes. If both parents are healthy, offspring has 0.9% chance of developing diabetes. The environmental factors include many factors such as excessive caloric intake, lack of physical exercise, obesity, stress, and drug abuse, which are rapidly increasing with economic growth. Defective insulin secretion from pancreatic beta cells and defective insulin action on its target cells, i.e., insulin resistance are all observed in type 2 diabetes. It is not yet clear which of them is of primary importance.

It is known that the most effective therapy for diabetes is to prevent complications by administering an excellent hypoglycemic agent at the early stage of development. Oral hypoglycemic agents for the treatment of diabetes include sulfonylureas, biguanides, acarbose, etc. Among them, the second generation of sulfonylureas is generally used, because of faster onset of action and strong hypoglycemic effect, and it is used in adult diabetic patients who are not obese. Biguanide and acarbose are commonly used in obese diabetic patients who are overweight. One of the biggest differences between biguanide and acarbose with sulfonylureas is the low frequency of hypoglycemic induction.

An ideal hypoglycemic agent is a safe oral drug that exhibits rapid efficacy to prevent a postprandial blood glucose increase, loses the efficacy in a short time not to cause unnecessary hypoglycemia, and also corrects the metabolic abnormalities associated with diabetes. Now, there is an urgent demand for the development of these hypoglycemic agents, and methods of treating diabetes by using traditional medicines or natural materials attract a lot of attention.

At present, there is an effort to develop a therapeutic agent capable of lowering the side effects of therapeutic agents for insulin-independent diabetes and treating insulin-dependent and independent diabetes at the same time. Traditionally, herbal medicines used in oriental medicine have been known to have various therapeutic effects while having low toxicity. To date, there have been reports of diabetes treatment of using dozens of herbal medicines singly or in combination, and it is also reported that both insulin-dependent and independent diabetes may be treated at the same time.

*Hypoxylon truncatum* belongs to the phylum Ascomycota, the class Sordariomycetes, the order Xylariales, the family Xylariaceae, the genus *Hypoxylon*, and its fruiting body has a semicircular or irregularly distorted semicircular shape with a width of 4 mm~5 mm. Chemical structures of hypoxylonol-C and F isolated from *Hypoxylon truncatum* were first reported in 2012, (Miyuki Fukai et al., Journal of Natural Products 2012, 75, 22-25.), and researchers reported their physiological activities, in which hypoxylonol-C has an antiangiogenic effect (Miyuki Fukai et al., Journal of Natural Products 2014, 77, 1065-1068).

However, there have been no reports regarding stimulation of insulin secretion by *Hypoxylon truncatum* extract, and the present inventors found that the *Hypoxylon truncatum* extract and components thereof have insulin secretion-stimulating effects, thereby completing the present disclosure.

SUMMARY

An aspect provides a composition for stimulating insulin secretion from cells, the composition including any stereoisomer selected from the group consisting of Formulae I, II, and III, a solvate or hydrate thereof, or a mixture thereof, or a physiologically acceptable salt thereof.

Another aspect provides a *Hypoxylon* sp. mushroom extract including any stereoisomer selected from the group consisting of Formulae I, II, and III, a solvate or hydrate thereof, or a mixture thereof, or a physiologically acceptable salt thereof.

Still another aspect provides a method of stimulating insulin secretion from cells, the method including contacting the composition or the extract with cells.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
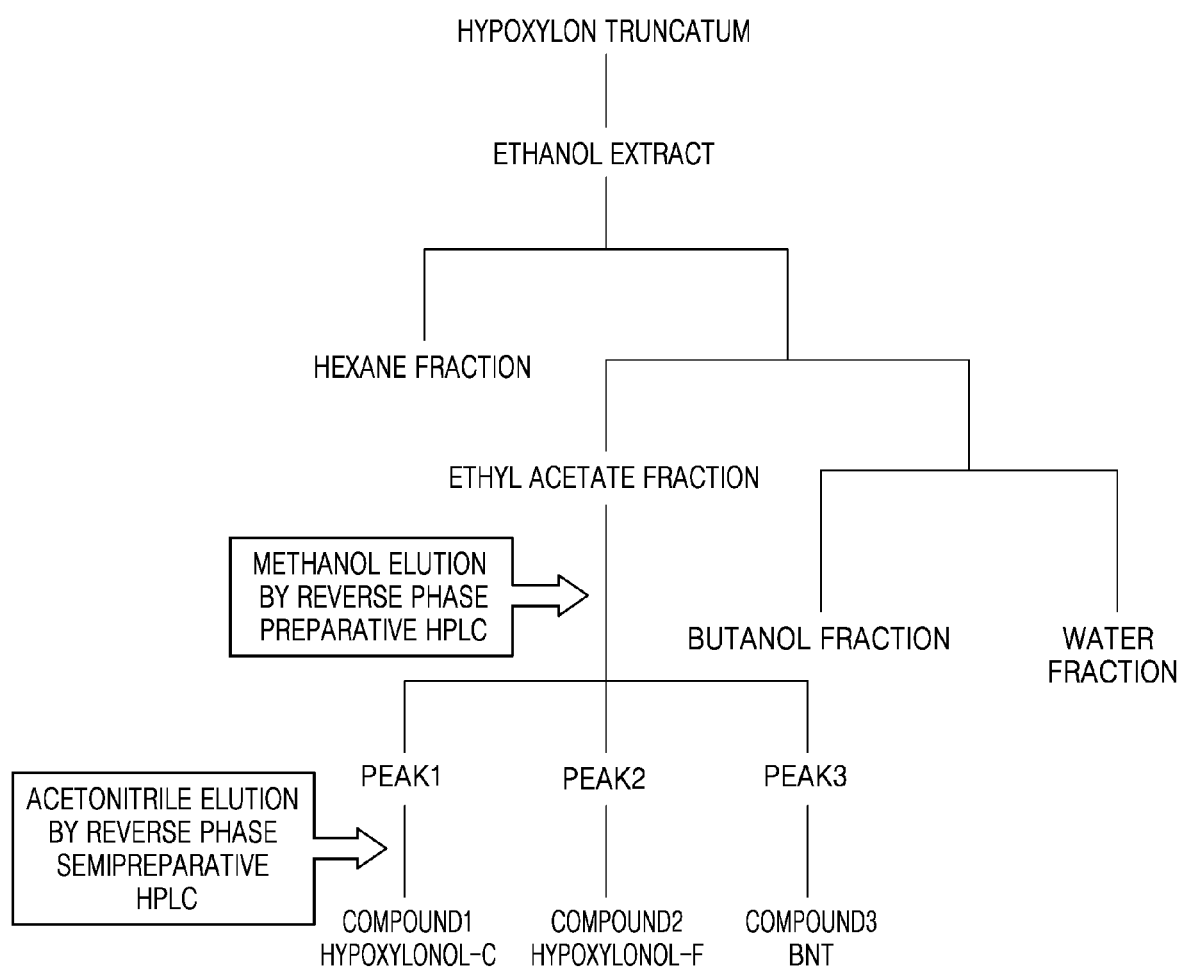
FIG. 1 is a schematic illustration showing preparation procedures of a *Hypoxylon truncatum* extract and fractions thereof.

An aspect provides a composition for stimulating insulin secretion from cells, the composition including any stereoisomer selected from the group consisting of Formulae I, II, and III, a solvate or hydrate thereof, or a mixture thereof, or a physiologically acceptable salt thereof:

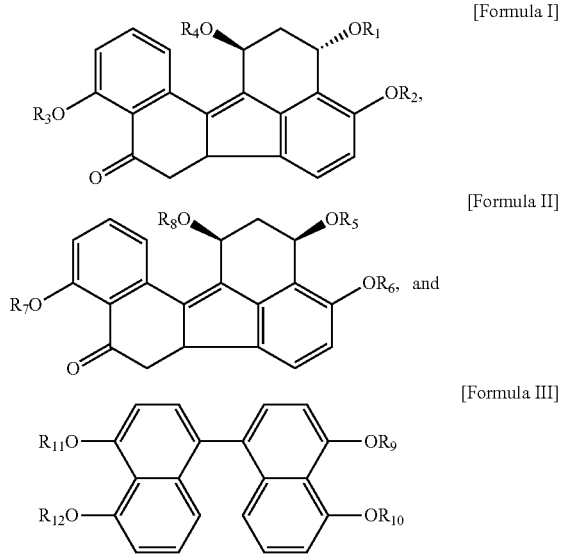

[Formula I]

[Formula II]

[Formula III]

(in Formula I, II, and III, $R_1$, $R_2$, $R_3$, $R_4$, $R_5$, $R_6$, $R_7$, $R_8$, $R_9$, $R_{10}$, $R_{11}$, and $R_{12}$ are each independently H or ($C_1$-$C_6$)-alkyl.)

In the composition, $R_1$ and $R_5$ may be each independently H or ($C_1$-$C_6$)-alkyl, and $R_2$, $R_3$, $R_4$, $R_6$, $R_7$, $R_8$, $R_9$, $R_{10}$, $R_{11}$, and $R_{12}$ may be each independently H. ($C_1$-$C_6$)-alkyl may be ($C_1$-$C_5$)-alkyl, ($C_1$-$C_4$)-alkyl, or ($C_1$-$C_3$)-alkyl.

In the composition, $R_1$ and $R_5$ may be each independently H, methyl, or ethyl.

In the composition, the compounds of Formula I, II, and III may exist at a weight ratio of 1.0: 0.20 to 0.60: 0.50 to 1.00. The weight ratio may be, for example, 1.0: 0.32 to 0.52: 0.65 to 0.85, or 1.0: 0.42: 0.75.

The composition may include the compound of Formula I, the compound of Formula II, or the compound of Formula III. The composition may include the compound of Formula I and the compound of Formula II; the compound of Formula I and the compound of Formula III; the compound of Formula II and the compound of Formula III; or the compound of Formula I, the compound of Formula II, and the compound of Formula III. In this regard, the composition may not include the compound not mentioned among the compounds of Formula I, II, and III. The mentioned compounds may exist in the above-described weight ratio. For example, regarding that "the compounds of Formula I, II, and III at a weight ratio of 1.0: 0.20 to 0.60: 0.50 to 1.00", when the composition include the compounds of Formula I and II; or the compounds of Formula I and III, a weight ratio may be 1.0: 0.20 to 0.60, and 1.0: 0.50 to 1.00, respectively.

In the composition, the cells may be pancreatic beta cells or insulin secretiong cells derived therefrom. The cells may be INS-1 cells.

The composition may be to prevent or treat diabetes. The diabetes may be type 1 or 2 diabetes.

The present disclosure includes all stereoisomers of the compound of Formula I, II, or III, salts thereof, and solvates thereof. With respect to each chiral center, independently of any other chiral centers, the compound of Formula I, II, or III may exist in S stereochemical configuration or substantially S stereochemical configuration, or in R stereochemical configuration or substantially R stereochemical configuration, or in a mixture of the S isomer and the R isomer at any ratio. The present disclosure includes all possible enantiomers and diastereoisomers and mixtures of two or more stereoisomers, for example, mixtures of enantiomers and/or diastereoisomers at any ratio. Therefore, the compound according to the present disclosure which may exist as an enantiomer may exist in an enantiomerically pure form, including both the left-handed enantiomer and the right-handed enantiomer, and in a mixture of both enantiomers in any ratio, including racemates. In a specific embodiment of the present invention, the compound which may exist in a mixture of two or more stereoisomer forms is a pure or substantially pure individual stereoisomer. Preparation of the individual stereoisomer may be performed by a common method, for example, by chromatography or crystallization, by separation of a mixture of isomers, by using a stereochemically homogeneous starting material in synthesis, or by stereoselective synthesis. Optionally, before separation of stereoisomers, derivatization may be performed. Separation of a mixture of stereoisomers may be performed in the process of the compound of Formula I or in the process of a starting material or an intermediate material during synthesis. Further, the present invention includes all tautomers of the compound of Formula I, II, or III, salts thereof, and solvates thereof.

When the compound of Formula I, II, or III include one or more acidic and/or basic groups, i.e., salt-forming groups, the present disclosure includes physiologically or toxicologically acceptable salts, i.e., non-toxic salts, particularly, pharmaceutically acceptable salts thereof.

The composition may include all solvates of any stereoisomer selected from the group consisting of Formula I, II, and III, for example, adducts of hydrate or alcohol such as ($C_1$-$C_4$)-alkanol, active metabolites of the compound of Formula I, and pro-drugs and derivatives of the compound of Formula I, II, or III, which may be converted into a compound that may not exhibit pharmaceutical activity in vitro, but may exhibit pharmaceutical activity in vivo, for example, ester or amide of carboxylic acid.

The composition may further include an excipient or a carrier which is acceptable for use in cosmetics, pharmaceuticals, or foods. The composition may be a pharmaceutical, food, or cosmetic composition.

The excipient or carrier may be a diluent, a disintegrant, a binder, a lubricant, or a combination thereof. The excipient may be microcrystalline cellulose, lactose, low-substituted hydroxycellulose, or a combination thereof. The disintegrant may be sodium starch glycolate, calcium monohydrogen phosphate anhydrous, or a combination thereof. The binder may be polyvinylpyrrolidone, low-substituted hydroxypropylcellulose, hydroxypropylcellulose, or a combination thereof. The lubricant may be magnesium stearate, silicon dioxide, talc, or a combination thereof.

The composition may be formulated into an oral or parenteral formulation. The oral formulation may include granules, powders, solutions, tablets, capsules, dry syrups, or combinations thereof. The parenteral formulation may include injectable formulations or external preparations for skin. The external preparations for skin may include creams, gels, ointments, skin emulsions, skin suspensions, transdermal patches, drug-containing bandages, lotions, or packs including mask packs.

The pharmaceutical composition may further include a pharmaceutical auxiliary agent such as a preservative, a stabilizer, a hydrating agent or an emulsifying accelerator, a salt and/or buffer for controlling osmotic pressure, and other therapeutically useful substances. The pharmaceutical composition may be formulated into various oral or parenteral dosage forms according to an ordinary method.

Examples of the oral dosage forms may include tablets, pills, hard and soft capsules, liquids, suspensions, emulsions, syrups, powders, fine granules, granules, pellets, etc., and these formulations may include surfactants, diluents (e.g., lactose, dextrose, sucrose, mannitol, sorbitol, cellulose, and glycine), lubricants (e.g., silica, talc, stearic acid, and magnesium or calcium salt thereof and polyethylene glycol), in addition to active ingredients. Tablets may also include binders such as magnesium aluminum silicate, starch paste, gelatin, tragacanth, methyl cellulose, sodium carboxymethyl cellulose, and polyvinylpyrrolidine, and if necessary, may include pharmaceutical additives such as disintegrants such as starch, agar, alginic acid or a sodium salt thereof, absorbents, coloring agents, flavoring agents, and sweetening agents. The tablets may be prepared by a common mixing, granulating, or coating method. The parenteral dosage form may include transdermal formulations, for example, injectable formulations, drops, ointments, lotions, gels, creams, sprays, suspensions, emulsions, suppositories, patches, etc., but is not limited thereto.

The pharmaceutical composition according to an embodiment of the present disclosure may be administered parenterally, rectally, topically, transdermally, or subcutaneously. The pharmaceutical composition according to an embodiment of the present disclosure may be topically administered.

An administration dosage of the active ingredient may be determined within the level of those skilled in the art, and a daily administration dose of the drug depends on various factors such as the degree of progression of obesity, the time of onset, age, health condition, complications, etc. of a subject to be administered, and the composition of the present invention may be generally administered once or several times a day in a dose of 1 µg/kg to 200 mg/kg, preferably 50 µg/kg to 50 mg/kg per adult. The administration dose is not intended to limit the scope of the present disclosure in any way.

The composition may include a *Hypoxylon* sp. *mushroom* extract including any stereoisomer selected from the group consisting of Formulae I, II, and III, a mixture thereof, or a physiologically acceptable salt thereof.

*Hypoxylon* sp. *mushroom* may be, for example, *Hypoxylon truncatum*, *Hypoxylon fuscum*, *Hypoxylon fragiforme*, or *Hypoxylon tinctor*.

The extract may be extracted by a method including contacting the *Hypoxylon* sp. *mushroom* with water, an organic solvent, or a mixture thereof. The contacting may be performed at 10° C. to reflux temperature. The temperature may be room temperature, 15° C. to reflux temperature, 25° C. to reflux temperature, 40° C. to reflux temperature, 50° C. to reflux temperature, or 25° C. to 70° C.

The organic solvent may be an aqueous or non-aqueous organic solvent. The organic solvent may be $(C_1-C_6)$-alcohol, $R_{13}$—COO—$R_{14}$, wherein $R_{13}$ and $R_{14}$ are each independently $(C_1-C_6)$-alkyl, $(C_4-C_{12})$-alkane, acetone, ethyl methyl ketone, acetonitrile, carbon tetrachloride ($CCl_4$), chloroform ($CHCl_3$), dichloromethane ($CH_2Cl_2$), or a mixture thereof. $(C_1-C_6)$-alcohol may be $(C_1-C_3)$-alcohol. The alcohol may be methanol, ethanol, isopropanol, or butanol. In $R_{13}$—COO—$R_{14}$, $R_{13}$ and $R_{14}$ may be each independently $(C_1-C_3)$-alkyl, $(C_1-C_2)$-alkyl, or methyl. $R_{13}$—COO—$R_{14}$ may be ethyl acetate. The $(C_4-C_{12})$-alkane may be $(C_4-C_{10})$-alkane, $(C_6-C_8)$-alkane, or hexane. The solvent may be acetone, ethyl methyl ketone, methanol, ethanol, carbon tetrachloride, chloroform, dichloromethane, or a mixed solvent of ethanol and dichloromethane.

In a specific embodiment, the extract may be an alcohol extract obtained by contacting the *Hypoxylon* sp. *mushroom* with $(C_1-C_6)$-alcohol.

In a specific embodiment, the extract may be a fraction or a residue thereof which is obtained by fractionating the extract with a $R_{13}$—COO—$R_{14}$ solvent, wherein $R_{13}$ and $R_{14}$ is each independently $(C_1-C_6)$-alkyl. The extract may be a fraction obtained as follows: the extract is fractionated with a $(C_4-C_{12})$-alkane solvent to obtain a fraction, and a residue remaining after removing the fraction is fractionated with a $R_{13}$—COO—$R_{14}$ solvent, wherein $R_{13}$ and $R_{14}$ is each independently $(C_1-C_6)$-alkyl, thereby obtaining the fraction. In a specific embodiment, the extract may be a fraction obtained as follows: the alcohol extract is dissolved in an aqueous solution or water to obtain an aqueous solution, this aqueous solution is contacted with $(C_4-C_{12})$-alkane, an aqueous solution or water layer, which remains after removing an alkane layer, with $R_{13}$—COO—$R_{14}$ wherein $R_{13}$ and $R_{14}$ is each independently $(C_1-C_6)$-alkyl, thereby obtaining the fraction. The $(C_1-C_6)$-alcohol may be $(C_1-C_4)$-alcohol, $(C_1-C_3)$-alcohol, ethanol, or methanol. The $(C_4-C_{12})$-alkane may be $(C_4-C_{10})$-alkane, $(C_6-C_8)$-alkane, or hexane. In $R_{13}$—COO—$R_{14}$, $R_{13}$ and $R_{14}$ may be each independently $(C_1-C_3)$-alkyl, ethyl, or methyl. The fraction may be a fraction obtained as follows: the *Hypoxylon* sp. *mushroom* is contacted with ethanol to obtain a ethanol extract, the ethanol extract is dissolved in an aqueous solution or water to obtain a ethanol extract aqueous solution, the ethanol extract aqueous solution is contacted with hexane, removing a hexane layer to obtain a remaining aqueous solution or water layer, which is then contacted with ethyl acetate, thereby obtaining the fraction. The aqueous solution may be a solution in which water is a solvent. The aqueous solution may be a solution containing electrolytes such as sodium chloride (e.g., a sodium chloride aqueous solution including saline solution) or sugars.

A contacting time may differ depending on an amount of the sample and a kind of the solvent to be used, and may be, for example, 6 hours to 48 hours, or 12 hours to 24 hours.

The obtained extract may be distilled under reduced pressure to remove the organic solvent, thereby obtaining the *Hypoxylon truncatum* extract. A temperature of the distillation under reduced pressure may differ depending on a kind of the solvent to be used, and may be, for example, 10° C. to 40° C. or 20° C. to 30° C.

Further, the *Hypoxylon truncatum* extract may be a fraction extract which is fractionated by using a polarity difference of solvents. The solvent used in the fractionation may be one or more selected from the group consisting of hexane, ethyl acetate, butanol, and water. For example, the solvent may be hexane or ethyl acetate. The fraction may be a fraction or a residue thereof obtained by fractionating the crude extract with hexane, ethyl acetate, and butanol in this order.

In a specific embodiment, *Hypoxylon truncatum* is contacted with ethanol to obtain a ethanol layer, and only the ethanol layer is subjected to distillation under reduced pressure to obtain a ethanol extract. This ethanol extract is dissolved in water, and then contacted with hexane to obtain a hexane layer. This hexane layer is subjected to distillation under reduced pressure to obtain a hexane fraction. An aqueous layer remaining after removing the hexane layer is contacted with ethyl acetate to obtain an ethyl acetate layer. The ethyl acetate layer is subjected to distillation under reduced pressure to obtain an ethyl acetate fraction. Water remaining during the preparation of the ethyl acetate fraction is contacted with butanol. A butanol layer is taken and distilled under reduced pressure to obtain a butanol fraction. Finally, a remaining water layer was subjected to distillation under reduced pressure to obtain a water fraction. As a result, the ethanol extract and hexane, ethyl acetate, n-butanol, and water fractions were obtained.

The fraction extracts may be isolated and purified by chromatography. The chromatography may be, for example, reverse phase preparative high performance liquid chromatography (Prep-HPLC).

Isolation conditions by reverse phase preparative HPLC may differ depending on the amount of the sample and a size of column to be used. The reverse phase preparative HPLC may be performed by preparing a reverse phase preparative column (Phenomenex Luna C18(2) column, a particle size of 10 μm, a column size of 250 mm×21.20 mm) in a liquid chromatography (Gilson Companion) system, dissolving a sample in an initial eluant and injecting the solution into the column, and then running an eluent in methanol:water from 50:50 to 100:0 for 60 minutes to 90 minutes.

Isolation conditions by the reverse phase semipreparative HPLC may differ depending on the amount of the sample and the reverse phase preparative column to be used. The reverse phase semipreparative HPLC may be performed by preparing a reverse phase preparative column (Phenomenex Gemini C6 Phenyl column, a particle size of 5 μm, a column size of 250 mm×10 mm) in a liquid chromatography (Gilson Companion) system, dissolving a sample in an initial eluant and injecting the solution into the column, and then running an eluent in acetonitrile:water from 50:50 to 100:0 for 60 minutes to 90 minutes.

Another aspect provides a *Hypoxylon* sp. *mushroom* extract including any stereoisomer selected from the group consisting of Formulae I, II, and III, a solvate or hydrate thereof, or a mixture thereof, or a physiologically acceptable salt thereof:

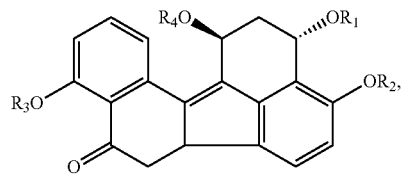

[Formula I]

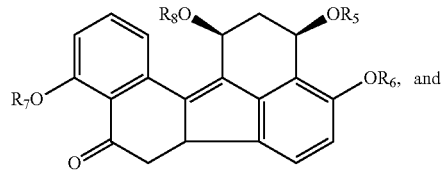

[Formula II]

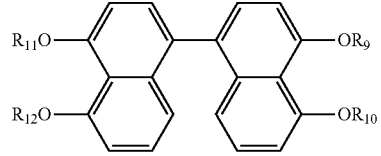

[Formula III]

(in Formula I, II, and III, $R_1$, $R_2$, $R_3$, $R_4$, $R_5$, $R_6$, $R_7$, $R_8$, $R_9$, $R_{10}$, $R_{11}$, and $R_{12}$ are each independently H or $(C_1-C_6)$-alkyl.)

The composition may include the compound of Formula I, the compound of Formula II, or the compound of Formula III. The composition may include the compound of Formula I and the compound of Formula II; the compound of Formula I and the compound of Formula III; the compound of Formula II and the compound of Formula III; or the compound of Formula I, the compound of Formula II, and the compound of Formula III. In this regard, the composition may not include the compound not mentioned among the compounds of Formula I, II, and III. The mentioned compounds may exist in the above-described weight ratio.

The extract may stimulate insulin secretion from cells. The cells may be pancreatic beta cells or insulin secretiong cells derived therefrom. The cells may be INS-1 cells.

The extract may be to prevent or treat diabetes. The diabetes may be type 1 or 2 diabetes.

Still another aspect provides an alcohol extract obtained by contacting the *Hypoxylon* sp. *mushroom* with $(C_1-C_6)$-alcohol. The extraction method and the use of the extract are the same as described above.

Still another aspect provides a water fraction or a composition including the water fraction, in which *Hypoxylon* sp. *mushroom* is contacted with $(C_1-C_6)$-alcohol to obtain an alcohol layer, from which alcohol is removed to obtain an alcohol extract, and this alcohol extract is dissolved in water to obtain an aqueous solution, and this aqueous solution is contacted with $(C_4-C_{12})$-alkane, an alkane layer is removed, and a remaining water layer is contacted with a $R_{13}$—COO—$R_{14}$ solvent, wherein $R_{13}$ and $R_{14}$ is each independently $(C_1-C_6)$-alkyl, and a water layer remaining after removing an ester layer is contacted with $(C_4-C_8)$-alcohol, and an alcohol layer is removed therefrom to obtain a remaining water layer, and then water is removed therefrom to obtain the water fraction. The $(C_1-C_6)$-alcohol may be $(C_1-C_4)$-alcohol, $(C_1-C_3)$-alcohol, ethanol, or methanol. The $(C_4-C_{12})$-alkane may be $(C_4-C_{10})$-alkane, $(C_6-C_8)$-alkane, or hexane. In $R_{13}$—COO—$R_{14}$, $R_{13}$ and $R_{14}$ may be each independently $(C_1-C_3)$-alkyl, ethyl, or methyl. The $(C_4-C_8)$-alcohol may be $(C_4-C_7)$-alcohol, $(C_4-C_6)$-alcohol, $(C_4-C_5)$-alcohol, or butanol. The fraction may be a water fraction obtained as follows: *Hypoxylon* sp. *mushroom* is contacted with ethanol to obtain a ethanol extract, the ethanol extract is dissolved in water to obtain a ethanol extract aqueous solution, the ethanol extract aqueous solution is contacted with hexane, a hexane layer is removed and a remaining water layer is contacted with ethyl acetate, an ethyl acetate layer is removed and a remaining water layer is contacted with butanol to obtain a butanol layer, and the butanol layer is removed, and from a remaining water layer, water is removed to obtain the water fraction.

Still another aspect provides a method of stimulating insulin secretion from cells, the method including contacting the composition or the extract with the cells.

The cells may be pancreatic beta cells. The contacting may be performed in vitro or in vivo, for example in human body, or in animal body other than human.

The contacting may include administering the composition or the extract to a subject. The subject may be a mammal including a human. The method may be to prevent or treat diabetes in the subject. The administering may be oral or parenteral administering.

A composition for stimulating insulin secretion from cells, including any stereoisomer selected from the group consisting of Formulae I, II, and III, a solvate or hydrate thereof, or a mixture thereof, or a physiologically acceptable salt thereof according to an aspect may be used to stimulate insulin secretion from cells.

A *Hypoxylon* sp. *mushroom* extract including any stereoisomer selected from the group consisting of Formulae I, II, and III, a solvate or hydrate thereof, or a mixture thereof, or a physiologically acceptable salt thereof according to another aspect may be used in the preparation of the composition.

A method of stimulating insulin secretion from cells according to still another aspect may be used to stimulate insulin secretion from cells.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items.

Hereinafter, the present invention will be described in more detail with reference to Examples. However, these Examples are for illustrative purposes only, and the scope of the present invention is not intended to be limited by these Examples.

EXAMPLE 1

Preparation of *Hypoxylon truncatum* Extract and Fractions Thereof

*Hypoxylon truncatum* used in the present disclosure was collected in Sogeum River, Yeongok-myeon, Gangneung-si, Gangwon-do, Korea, and extracted with organic solvents.

FIG. 1 is a schematic illustration showing preparation procedures of a *Hypoxylon truncatum* extract and fractions thereof. Detailed extraction procedures are as follows.

1. Preparation of Ethanol Extract

The whole body of *Hypoxylon truncatum* was ground in a mixer (NUC, Model no. NFM-8860), and 50 g thereof was put in 500 mL of 100% ethanol and left at room temperature for 24 hours. This procedure was repeated twice. This solution was filtered through a filter paper, and the resulting filtrate was distilled under reduced pressure to obtain 6.3 g of a crude extract (hereinafter, referred to as 'ethanol extract').

Figure 2:
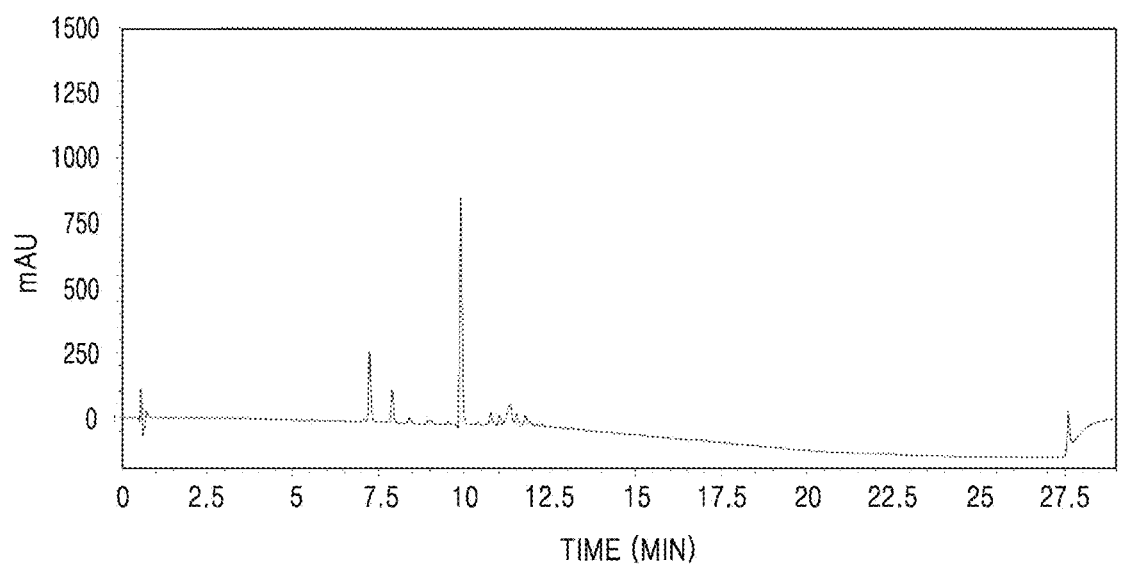
FIG. 2 is a chromatogram showing result of HPLC analysis of a ethanol extract of *Hypoxylon truncatum*.

FIG. 2 is a chromatogram showing the result of HPLC analysis of the ethanol extract of *Hypoxylon truncatum*. In FIGS. 2 to 6, HPLC analysis was performed by using Nexera X2 (Shimadzu, Japan) and a Phenomenex column EVO C18 with a particle size of 1.7 µm and a column size of 100 mm×2.1 mm under conditions of an acetonitrile gradient from 10% to 100% in water as an eluant for 25 minutes at a flow rate of 0.3 mL/min.

2. Preparation of Fractions (1) Hexane Fraction 5 g of 6.3 g of the *Hypoxylon truncatum* crude extract obtained in 1 was dissolved in 250 mL of water, and then mixed with 250 mL of hexane, and left at room temperature for 24 hours to separate a hexane layer. This procedure was repeated three times, and the resulting hexane layer was distilled under reduced pressure to obtain 107 mg of a hexane layer fraction (hereinafter, referred to as 'hexane fraction').

Figure 3:
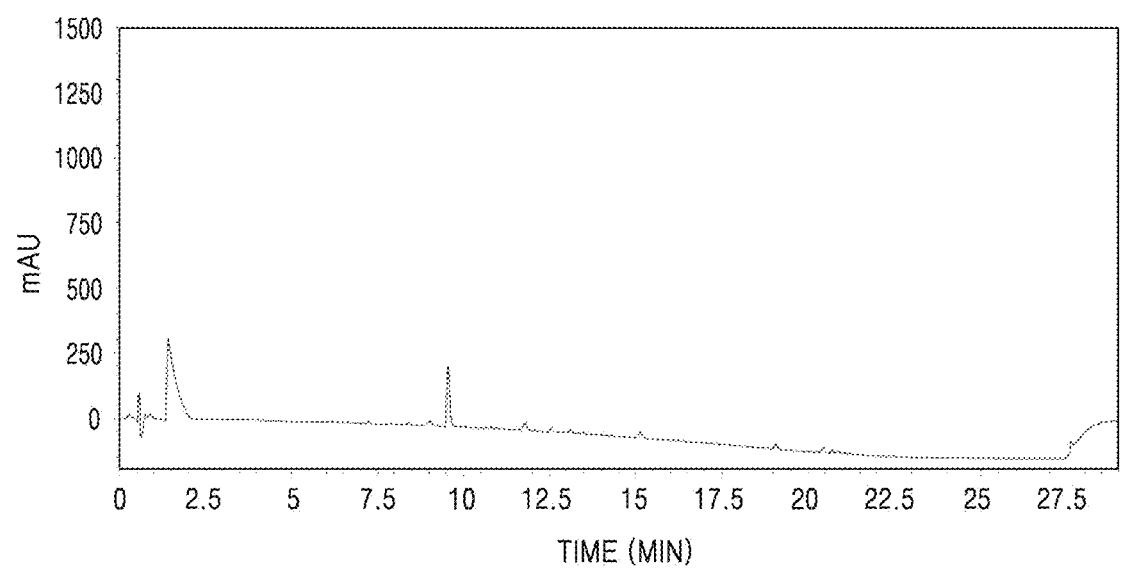
FIG. 3 is a chromatogram showing result of HPLC analysis of a hexane fraction of *Hypoxylon truncatum*.

FIG. 3 is a chromatogram showing the result of HPLC analysis of the hexane fraction of *Hypoxylon truncatum*.

(2) Ethyl Acetate Fraction

A water layer which remained after obtaining the hexane fraction in (1) was mixed with 250 mL of ethyl acetate, and left at room temperature for 24 hours to separate an ethyl acetate layer. This procedure was repeated three times, and the resulting ethyl acetate layer was distilled under reduced pressure to obtain 2 g of an ethyl acetate layer fraction (hereinafter, referred to as 'ethyl acetate fraction').

Figure 4:
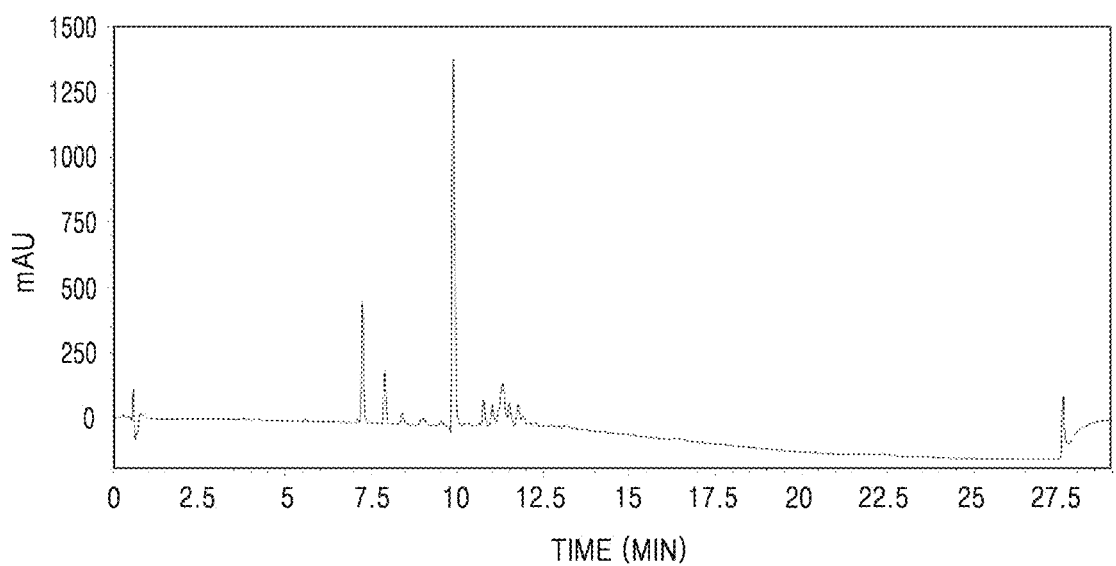
FIG. 4 is a chromatogram showing result of HPLC analysis of an ethyl acetate fraction of *Hypoxylon truncatum*.

FIG. 4 is a chromatogram showing the result of HPLC analysis of the ethyl acetate fraction of *Hypoxylon truncatum*.

(3) Butanol Fraction

A water layer which remained after fractionating the ethyl acetate layer in (2) was mixed with 250 mL of n-butanol, and left at room temperature for 24 hours to separate a butanol layer. This procedure was repeated twice, and the resulting butanol layer was distilled under reduced pressure to obtain 1.5 g of a butanol layer fraction (hereinafter, referred to as 'butanol fraction').

Figure 5:
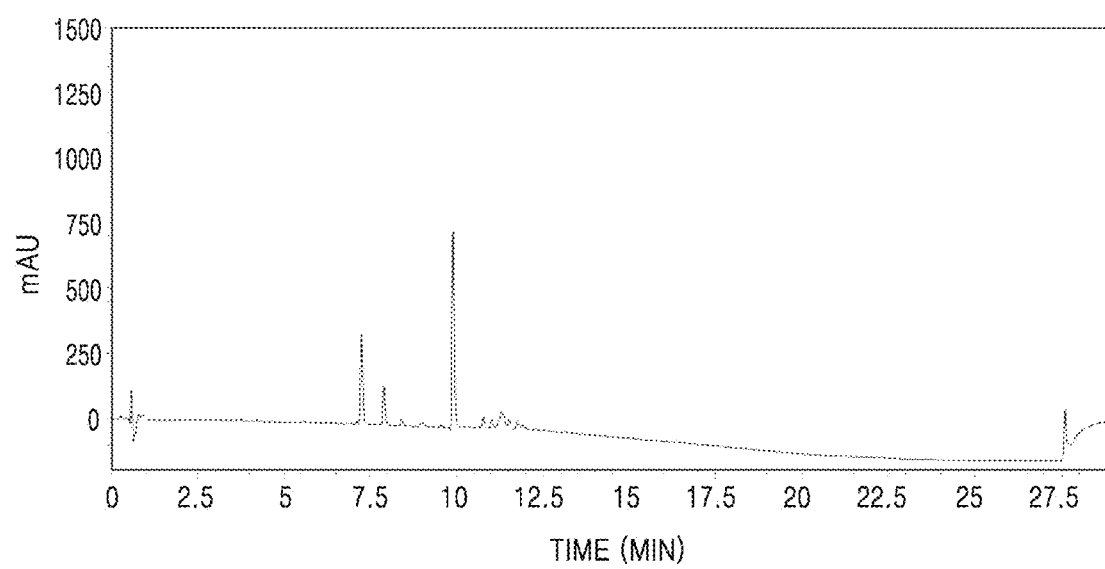
FIG. 5 is a chromatogram showing result of HPLC analysis of a butanol fraction of *Hypoxylon truncatum*.

FIG. 5 is a chromatogram showing the result of HPLC analysis of the butanol fraction of *Hypoxylon truncatum*.

(4) Water Fraction

A water layer which remained after fractionating the butanol layer in (3) was distilled under reduced pressure to obtain 1.2 g of a water layer fraction (hereinafter, referred to as 'water fraction').

Figure 6:
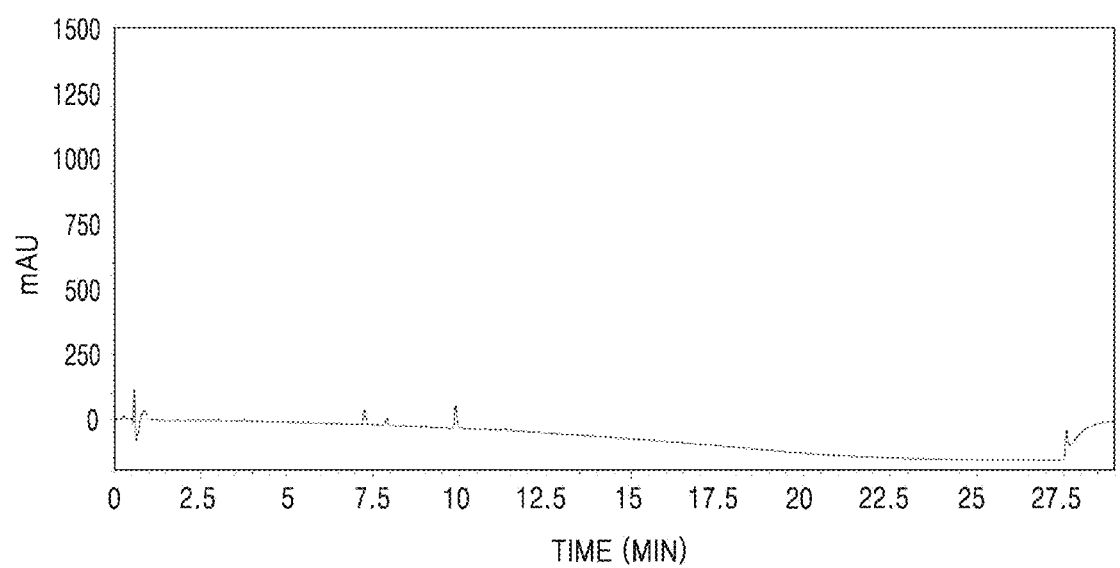
FIG. 6 is a chromatogram showing result of HPLC analysis of a water fraction of *Hypoxylon truncatum*.

FIG. 6 is a chromatogram showing the result of HPLC analysis of the water fraction of *Hypoxylon truncatum*.

(5) Isolation of hypoxylonol-C, hypoxylonol-F, and BNT

Three compounds including hypoxylonol-C were separated from the ethyl acetate layer fraction of the *Hypoxylon truncatum* crude extract described in (3).

In detail, the fraction was eluted in a reverse phase preparative HPLC (Phenomenex Luna C18(2) column, a particle size of 10 µm, a column size of 250 mm×21.20 mm) under conditions of a methanol gradient from 50% to 100% in water as an eluant for 60 minutes to 90 minutes at a flow rate of 8 mL/min. As a result, three peaks appeared at UV 230 nm in the obtained chromatogram (FIG. 4). Among the peaks, fractions corresponding to peaks 1 to 3 were eluted in a reverse phase semipreparative HPLC (Phenomenex Gemini C6 Phenyl column, a particle size of 5 μm, a column size of 250 mm×10 mm) under conditions of an acetonitrile gradient from 50% to 100% in water as an eluant for 60 minutes to 90 minutes at a flow rate of 4 mL/min. As a result, 158 mg of hypoxylonol-C, 67 mg of hypoxylonol-F, and 119 mg of BNT compound were confirmed in the obtained chromatogram.

The structures of the compounds were confirmed by nuclear magnetic resonance spectrometer (NMR) and mass spectroscopy. The structures of the compounds were confirmed by $^1$H-NMR and $^{13}$C-NMR (Bruker AVACE III 400 MHz spectrometer, Bruker, Germany). Chemical structural formulae and $^1$H-NMR and $^{13}$C-NMR data of the isolated compounds are as follows:

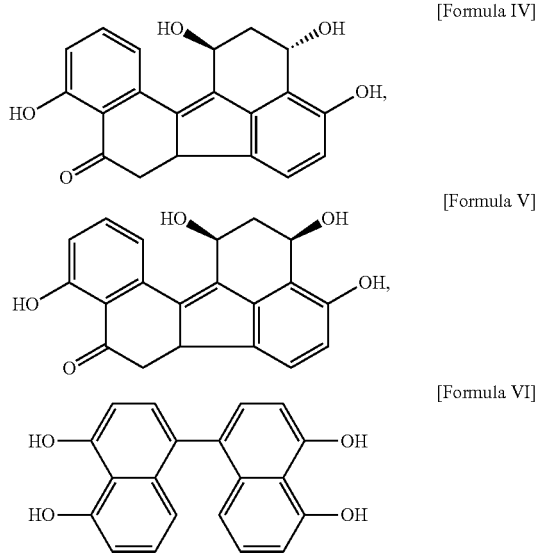

[Formula IV]

[Formula V]

[Formula VI]

Formula IV compound: Hypoxylonol-C $^1$H-NMR (400 MHz, Acetone-$d_6$) δ12.6 (s, 1H, OH-9), 8.61 (s, 1H, OH-4), 7.54 (t, 1H, H-11), 7.48 (dd, 1H, H-12), 7.28 (d, 1H, H-6), 6.84 (dd, 1H, H-10), 6.68 (d, 1H, H-5), 5.59 (dd, 1H, H-1), 5.48 (m, 1H, H-3), 5.14 (brd, 1H, OH-3), 4.28 (s, 1H, OH-1), 4.11 (dd, 1H, H-6b), 3.38 (dd, 1H, H-7), 2.47 (dt, 1H, H-2), 2.31 (dd, 1H, H-7), 2.14 (ddd, 1H, H-2)

$^{13}$C-NMR (100 MHz, Acetone-$d_6$) δ 205.9 (C-8), 163.5 (C-9), 155.7 (C-4), 144.1 (C-12d), 139.5 (C-12a), 138.1 (C-12c), 137.6 (C-12b), 137.4 (C-11), 136.4 (C-6a), 123.5 (C-6), 120.6 (C-3a), 118.9 (C-12), 117.0 (C-10), 115.6 (C-8a), 114.4 (C-5), 65.4 (C-3), 65.7 (C-1), 59.7 (C-6b), 43.6 (C-7), 42.3 (C-2)

ESI-MS m/z 335.0 [M–H]$^-$.

Formula V compound: Hypoxylonol-F $^1$H-NMR (400 MHz, Acetone-$d_6$) δ12.6 (s, 1H, OH-9), 7.52 (t, 1H, H-11), 7.48 (dd, 1H, H-12), 7.29 (d, 1H, H-6), 6.82 (dd, 1H, H-10), 6.69 (d, 1H, H-5), 5.38 (d, 1H, H-1), 5.36 (d, 1H, H-3), 4.09 (dddd, 1H, H-6b), 3.39 (dd, 1H, H-7), 2.47 (dt, 1H, H-2), 2.34 (dd, 1H, H-7), 2.24 (dt, 1H, H-2)

$^{13}$C-NMR (100 MHz, Acetone-$d_6$) δ 206.3 (C-8), 163.6 (C-9), 155.7 (C-4), 144.3 (C-12d), 139.5 (C-12a), 139.1 (C-12c), 137.5 (C-12b), 137.2 (C-11), 136.7 (C-6a), 123.8 (C-6), 121.0 (C-3a), 120.9 (C-12), 117.0 (C-10), 115.8 (C-8a), 114.7 (C-5), 67.0 (C-3), 65.2 (C-1), 50.2 (C-6b), 43.8 (C-7), 43.3 (C-2)

ESI-MS m/z 335.0 [M–H]$^-$.

Formula VI compound: BNT, 1,1'-binaphthalene-4,4',5,5'-tetrol $^1$H-NMR (400 MHz, DMSO-$d_6$) δ11.04 (brd, 4H, OH-4, 5), 7.16 (d, 2H, H-7), 7.07 (t, 2H, H-2), 6.83 (d, 2H, H-3), 6.72 (dd, 2H, H-6), 6.59 (d, 2H, H-8)

$^{13}$C-NMR (100 MHz, DMSO-$d_6$) δ 154.4 (C-5), 153.7 (C-4), 135.7 (C-8a), 129.3 (C-1), 128.8 (C-7), 126.9 (C-2), 117.4 (C-8), 114.5 (C-4a), 108.5 (C-6), 108.1 (C-3)

ESI-MS m/z 317.1 [M–H]$^-$.

EXAMPLE 2

Examination of Physiological Activities of *Hypoxylon truncatum* Extract and Fractions Thereof 1. Insulin-stimulating activity of *Hypoxylon truncatum* extract and fractions thereof.

(1) Measurement of cytotoxicity against INS-1 Cells

A cell line INS-1 (Biohermes, Shanghai, China) is a rat insulinoma, and has ability to secrete insulin.

Cultured INS-1 cells were cultured in RPMI1640 medium (Cellgro, Manassas, Va., USA) supplemented with 10% fetal bovine serum (FBS), 100 unit/mL of penicillin G, 100 μg/mL of streptomycin, 10 mM Hepes, 2 mM L-glutamine, 1 mM sodium pyruvate, and 0.05 mM 2-merchapto ethanol in an incubator maintained at 37° C. and 95% air/5% carbon dioxide. Among the above-mentioned ingredients, the reagents of which manufacturers were not mentioned were purchased from Gibco BRL, Life Technologies. The cultured INS-1 cells were dispensed at a density of 1×10$^4$ per well in 100 μL of the same medium in a 96-well plate, and cultured for 24 hours to stabilize the cells. Thereafter, the *Hypoxylon truncatum* extract, hexane fraction, ethyl acetate fraction, butanol fraction, water fraction, hypoxylonol-C, hypoxylonol-F, and BNT were added thereto at predetermined concentrations, and cultured for 24 hours. Then, 10 μL of CCK-8 (Dojindo Laboratories, Japan) reagent was added to each well, and cultured at 37° C. 1 hour later, absorbance at 450 nm was measured by using a BIO-TEK (Winooski, Vt., USA) microplate reader to measure cell viability. The predetermined concentrations are as follows: concentrations of *Hypoxylon truncatum* extract, hexane fraction, ethyl acetate fraction, butanol fraction, and water fraction were 2.5 μg/mL, 5.0 μg/mL, and 10.0 μg/mL. The concentration of the single compound was 1.0 μM, 2.5 μM, and 5.0 μM.

Table 1 shows results of a cytotoxicity test of *Hypoxylon truncatum* extract, hexane fraction, ethyl acetate fraction, butanol fraction, water fraction, hypoxylonol-C, hypoxylonol-F, and BNT against INS-1 which is a rat insulinoma cell line.

TABLE 1

| Section | Concentration (μg/mL) | Cell viability (%) |
|---|---|---|
| *Hypoxylon truncatum* extract (ethanol extract) | 2.5 | 94.8 ± 1.1 |
| | 5.0 | 101.3 ± 2.7 |
| | 10.0 | 91.0 ± 5.0 |
| Hexane fraction | 2.5 | 99.7 ± 3.6 |
| | 5.0 | 91.8 ± 1.9 |
| | 10.0 | 98.9 ± 3.5 |
| Ethyl acetate fraction | 2.5 | 98.0 ± 2.6 |
| | 5.0 | 97.1 ± 1.8 |
| | 10.0 | 101.0 ± 3.0 |
| Butanol fraction | 2.5 | 99.2 ± 0.8 |
| | 5.0 | 94.4 ± 3.0 |
| | 10.0 | 92.4 ± 3.2 |

TABLE 1-continued

| Section | Concentration (μg/mL) | Cell viability (%) |
|---|---|---|
| Water fraction | 2.5 | 98.7 ± 0.7 |
|  | 5.0 | 93.8 ± 1.7 |
|  | 10.0 | 90.6 ± 3.2 |
| Hypoxylonol-C | 1.0 | 97.4 ± 1.7 |
|  | 2.5 | 96.4 ± 1.4 |
|  | 5.0 | 97.3 ± 3.0 |
| Hypoxylonol-F | 1.0 | 96.2 ± 4.5 |
|  | 2.5 | 97.3 ± 4.6 |
|  | 5.0 | 96.1 ± 0.9 |
| BNT | 1.0 | 100.3 ± 3.6 |
|  | 2.5 | 100.1 ± 2.1 |
|  | 5.0 | 106.6 ± 2.9 |

In Table 1, cell viability was calculated by the following equation:

Cell viability (%)=NB×100, wherein A represents absorbance of a non-sample added group and B represents absorbance of a sample-added group.

As shown in Table 1, *Hypoxylon truncatum* extract, respective fractions, hypoxylonol-C, hypoxylonol-F, and BNT showed no cytotoxicity against INS-1 cells.

(2) Measurement of Effect on Insulin Secretion of INS-1 cells

The cultured INS-1 cells were dispensed at a density of 5×10$^5$ per well in 2 mL of the same medium in a 12-well plate, and then cultured for 24 hours in the same manner as described in (1) to stabilize the cells. Thereafter, the cells were washed twice with 2 ml of Krebs-Ringer buffer which was prepared by mixing 114 mM sodium chloride (NaCl), 4.4 mM potassium chloride (KCl), 1 mM magnesium sulfate (MgSO$_4$), 1.28 mM calcium chloride (CaCl$_2$), 29.5 mM sodium bicarbonate (NaHCO$_3$), 10 mM Hepes (Gibco BRL Life Technologies), and 0.1% bovine serum albumin (BSA) and adjusting a hydrogen ion concentration at pH 7.4.

Thereafter, 2 ml of the Krebs-Ringer buffer was added to the washed well, cultured for 1 hour, and then cultured for 30 minutes in 1.8 mL of Krebs-Ringer buffer with the *Hypoxylon truncatum* extract, hexane fraction, ethyl acetate fraction, butanol fraction, water fraction, hypoxylonol-C, hypoxylonol-F, and BNT at predetermined concentrations. The predetermined concentrations are as follows: concentrations of the extract and the fractions were 2.5 μg/mL, 5 μg/mL, and 10 μg/mL. The concentration of the single compound was 1 μM, 2.5 μM, and 5 μM.

0.2 mL of Krebs-Ringer buffer containing 33 mM or 167 mM glucose was added to each well, and incubated for 1 hour. Thereafter, centrifugation was performed at 4° C. for 10 minutes at 12,000 rpm, and a supernatant was taken and quantity of insulin was measured by using a Rat insulin RIA kit (Gentaur Molecular Products, Belgium). Stimulation index (SI) was calculated by dividing a value measured at a high concentration of glucose, i.e., quantity of insulin secreted by stimulation of 16.7 mM glucose by a value measured at a low concentration of glucose, i.e., quantity of insulin secreted by stimulation of 3.3 mM glucose. Stimulation indices thus measured were shown in Table 2. As a positive control group, gliclazide was used at a concentration of 2.5 μM, 5.0 μM, 10 μM, or 20 μM.

TABLE 2

| Section | Concentration (μg/ml) | Stimulation index (SI) |
|---|---|---|
| *Hypoxylon truncatum* extract (ethanol extract) | 2.5 | 1.5 ± 0.1 |
|  | 5.0 | 2.1 ± 0.0 |
|  | 10.0 | 2.3 ± 0.2 |
| Hexane fraction | 2.5 | 0.9 ± 0.0 |
|  | 5.0 | 1.1 ± 0.0 |
|  | 10.0 | 1.0 ± 0.0 |
| Ethyl acetate fraction | 2.5 | 3.6 ± 0.2 |
|  | 5.0 | 3.6 ± 0.2 |
|  | 10.0 | 6.4 ± 0.1 |
| Butanol fraction | 2.5 | 1.0 ± 0.1 |
|  | 5.0 | 1.0 ± 0.0 |
|  | 10.0 | 1.0 ± 0.2 |
| Water fraction | 2.5 | 0.9 ± 0.0 |
|  | 5.0 | 2.4 ± 0.0 |
|  | 10.0 | 4.6 ± 0.3 |
| Hypoxylonol-C | 1.0 | 6.3 ± 0.3 |
|  | 2.5 | 5.3 ± 0.1 |
|  | 5.0 | 6.1 ± 0.1 |
| Hypoxylonol-F | 1.0 | 7.1 ± 0.4 |
|  | 2.5 | 7.7 ± 0.3 |
|  | 5.0 | 10.6 ± 0.3 |
| BNT | 1.0 | 6.7 ± 0.0 |
|  | 2.5 | 7.4 ± 0.0 |
|  | 5.0 | 6.8 ± 0.2 |
| gliclazide | 2.5 | 6.1 ± 0.0 |
|  | 5.0 | 5.7 ± 0.0 |
|  | 10.0 | 6.1 ± 0.1 |
|  | 20.0 | 9.3 ± 0.0 |

As shown in Table 2, INS-1 cells secreted insulin in the presence of the *Hypoxylon truncatum* extract, hexane fraction, ethyl acetate fraction, butanol fraction, water fraction, hypoxylonol-C, hypoxylonol-F, and BNT in a concentration-dependent manner. Particularly, in the presence of 5 μM hypoxylonol-F, INS-1 cells showed SI value similar to SI value in the presence of 20 μM gliclazide as the positive control.

2. Protecting Effect of Mushroom Extract and Ingredient on Pancreatic Toxicity (1) Protecting Effect on Pancreatic Toxicity The cell line INS-1 (Biohermes, Shanghai, China) was used to evaluate a protecting effect on pancreatic toxicity as follows.

INS-1 cells were cultured in RPMI1640 medium (Cellgro, Manassas, USA) supplemented with 10% fetal bovine serum (FBS), 100 unit/mL of penicillin G, 100 μg/mL of streptomycin, 10 mM Hepes, 2 mM L-glutamine, 1 mM sodium pyruvate, and 0.05 mM 2-merchapto ethanol in an incubator maintained at 37° C. and 95% air/5% carbon dioxide. Among the above-mentioned ingredients, the reagents of which manufacturers were not mentioned were purchased from Gibco BRL, Life Technologies.

The cultured INS-1 cells were dispensed at a density of 1×10$^4$ per well in 100 μL of the same medium in a 96-well plate, and cultured for 24 hours under the same conditions to stabilize the cells. Thereafter, the *Hypoxylon truncatum* extract, hexane fraction, ethyl acetate fraction, butanol fraction, water fraction, hypoxylonol-C, hypoxylonol-F, and BNT were added thereto at predetermined concentrations, and cultured in 90 μL of the same medium for 2 hours. Then, 10 μL (final concentration of 50 μM) of 500 μM streptozotocin in the same medium was added and cultured for 24 hours. Then, 10 μL of CCK-8 (Dojindo Laboratories, Japan) reagent was added to each well, and cultured at 37° C. 1 hour later, absorbance at 450 nm was measured by using a BIO-TEK (Winooski, Vt., USA) microplate reader to measure cell viability. The predetermined concentrations are as follows: concentrations of the extract and the fractions were 0 µg/mL, 5 µg/mL, 10 µg/mL, 25 µg/mL, 50 µg/mL, and 100 µg/mL. The concentration of the single compound was 0 µM, 5 µM, 10 µM, 25 µM, 50 µM, and 100 µM. Results are shown in Table 3.

TABLE 3

| Section | Concentration (µg/ml) | Cell viability (%) |
| --- | --- | --- |
| Hypoxylon truncatum extract | 0 | 59.7 ± 2.5 |
|  | 5 | 74.8 ± 1.2 |
|  | 10 | 83.5 ± 3.0 |
|  | 25 | 90.4 ± 3.4 |
|  | 50 | 90.9 ± 2.7 |
|  | 100 | 40.5 ± 2.1 |
| Hexane fraction | 0 | 58.0 ± 1.8 |
|  | 5 | 82.7 ± 0.5 |
|  | 10 | 86.6 ± 3.0 |
|  | 25 | 86.7 ± 1.2 |
|  | 50 | 91.3 ± 1.2 |
|  | 100 | 91.1 ± 2.5 |
| Ethyl acetate fraction | 0 | 60.0 ± 0.9 |
|  | 5 | 82.3 ± 2.3 |
|  | 10 | 92.6 ± 1.8 |
|  | 25 | 95.8 ± 2.4 |
|  | 50 | 36.0 ± 1.2 |
|  | 100 | 44.2 ± 0.6 |
| Butanol fraction | 0 | 66.2 ± 0.8 |
|  | 5 | 72.3 ± 2.3 |
|  | 10 | 78.7 ± 2.3 |
|  | 25 | 88.9 ± 2.9 |
|  | 50 | 96.5 ± 3.3 |
|  | 100 | 70.8 ± 3.7 |
| Water fraction | 0 | 57.7 ± 1.6 |
|  | 5 | 74.4 ± 3.1 |
|  | 10 | 76.7 ± 2.6 |
|  | 25 | 88.9 ± 2.9 |
|  | 50 | 96.5 ± 3.3 |
|  | 100 | 70.8 ± 3.7 |
| Hypoxylonol-C | 0 | 54.3 ± 0.8 |
|  | 5 | 66.0 ± 0.9 |
|  | 10 | 75.6 ± 2.5 |
|  | 25 | 80.7 ± 1.5 |
|  | 50 | 85.7 ± 1.7 |
|  | 100 | 90.0 ± 2.5 |
| Hypoxylonol-F | 0 | 61.9 ± 1.8 |
|  | 5 | 70.1 ± 1.7 |
|  | 10 | 68.3 ± 3.2 |
|  | 25 | 70.0 ± 4.3 |
|  | 50 | 69.8 ± 3.8 |
|  | 100 | 71.6 ± 0.9 |
| BNT | 0 | 59.9 ± 0.9 |
|  | 5 | 73.5 ± 3.0 |
|  | 10 | 76.8 ± 4.5 |
|  | 25 | 78.4 ± 1.5 |
|  | 50 | 81.5 ± 3.3 |
|  | 100 | 89.1 ± 1.6 |

As shown in Tale 3, the number of INS-1 cells was reduced to 50% or less by treatment of 50 µM streptozotocin, as compared with a non-treated group. The negative control group showed 100%. The Hypoxylon truncatum extract, hexane fraction, ethyl acetate fraction, butanol fraction, water fraction, hypoxylonol-C, hypoxylonol-F, and BNT significantly increased cell viability, which was reduced by addition of 50 µM streptozotocin, in a concentration-dependent manner. In particular, hypoxylonol-C and BNT at the concentration of 100 µM increased cell viability to 89% or more to show excellent effects.

(2) Protein Detection Test

The cultured INS-1 cells were dispensed at a density of $4 \times 10^5$ per well in 3 mL of the same medium as in (1) in a 6-well plate, and then cultured for 24 hours under the same conditions to stabilize the cells. Thereafter, hypoxylonol-C and BNT at 10 µM were added to 2.7 mL of the same medium and further cultured for 2 hours. 0.3 mL (final concentration of 50 µM) of 500 µM Streptozotocin in the same medium was added, and cultured for 24 hours. Then, cells were harvested and washed with phosphate-buffered saline (PBS) once, and then RIPA buffer (Cell Signaling, MA, USA) containing 1 mM phenylmethylsulfonyl fluoride was added, and left at 4° C. for 20 minutes. The reaction product was centrifuged at 12,000 rpm for 20 minutes to remove cell debris and to collect only a supernatant.

In a cell lysate separated from the supernatant obtained by removing cell debris, proteins were quantified by using a BCA protein detection kit (Thermo Scientific, Rockford, USA). 20 µg of the cell lysate per well was subjected to 10% sodium dodecyl sulfate polyacrylamide gel electrophoresis (SDS-PAGE) to separate denatured proteins. The separated proteins were transferred to a polyvinylidene difluoride membrane (PVDF membrane) (Merck Millipore, Germany). To prevent non-specific binding of antibodies to the membrane, the membrane was incubated in 5% skim milk at room temperature for 2 hours to block non-specific binding. Thereafter, the membrane was washed with TBST buffer (20 nM tris-HCl, 150 mM NaCl, and 0.05% Tween-20, pH 7.5) three times for each 10 minutes. Next, to measure expression levels of intracellular cleaved caspase-8, cleaved caspase-3, Bax, Bcl-2, PARP, and GAPDH, rabbit primary antibody (Cell Signaling, Danvers, USA) binding to each protein was diluted 1:1,000 and allowed to react at room temperature for 1 hour, followed by washing with TBST buffer for 10 minutes three times. Then, goat anti-rabbit IgG secondary antibody (Calbiochem, La Jolla, Calif., USA) was diluted 1:2,000 and allowed to react with the membrane at room temperature for 2 hours, followed by examination of proteins with an ECL detection kit (GE healthcare). Results are shown in FIG. 7.

Figure 7:
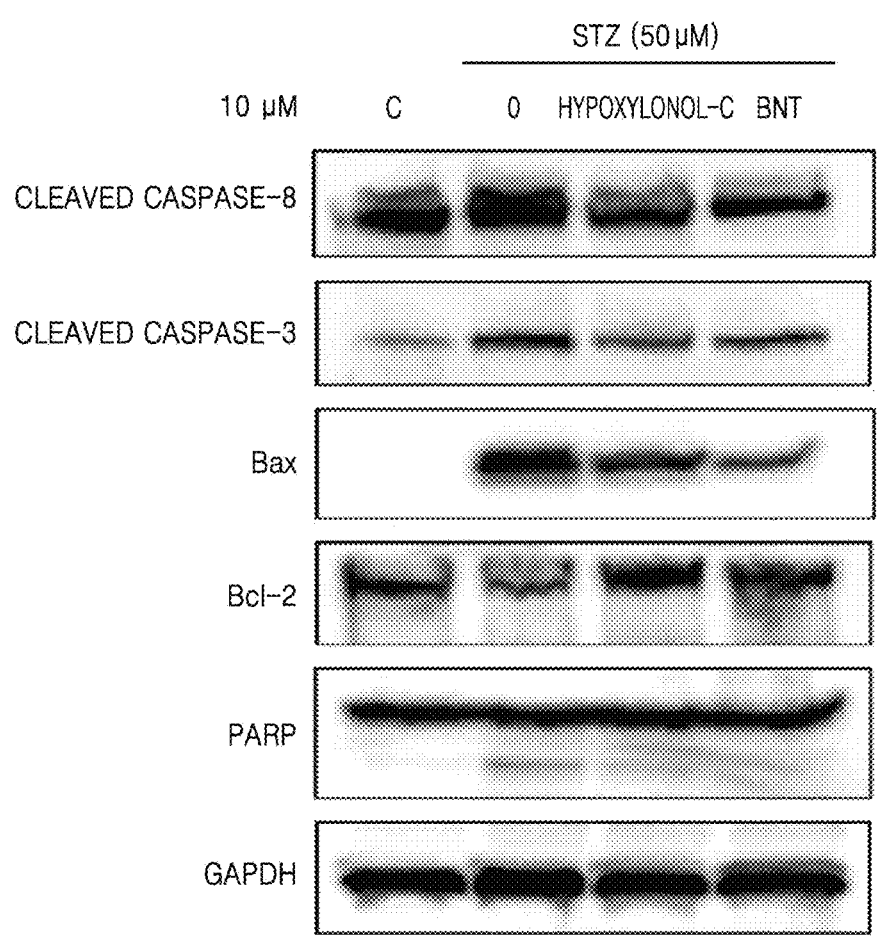
FIG. 7 is a photograph of Western blotting showing effects of streptozotocin, hypoxylonol-C and BNT on protein expression in INS-cells.

FIG. 7 is a photograph of Western blotting showing the effect of streptozotocin, hypoxylonol-C and BNT on protein expression in INS-cells. In FIG. 7, C represents a negative control group.

(3) Image-Based Cell Analysis

The cultured INS-1 cells were dispensed at a density of $4 \times 10^5$ per well in 3 mL of the same medium in a 6-well plate, and then cultured for 24 hours under the same conditions to stabilize the cells. Thereafter, hypoxylonol-C and BNT at a concentration of 10 µM were added to 2.7 mL of the same medium and further cultured for 2 hours. 0.3 mL (final concentration of 50 µM) of 500 µM Streptozotocin in the same medium was added, and cultured for 24 hours under the same conditions. Then, cells were collected by using trypsin, and washed with PBS once. The cells were suspended in 100 µL of Annexin binding buffer (composition: 100 mM HEPES, 140 mM NaCl, 25 mM $CaCl_2$, pH 7.4) at a density of $5 \times 10^5$ to $5 \times 10^6$ cells/mL, and then mixed with 5 µL of Annexin V Alexa Fluor 488, and fixed and stained at room temperature for 20 minutes in the dark room. The cell suspension was centrifuged to discard the supernatant. Precipitated cell pellets were re-suspended in 100 µL of Annexin binding buffer. 1 µL of propidium was added to the cell suspension and mixed well to fix and stain the cells at room temperature for 1 minute to 5 minutes in the dark room. Analysis of the stained cells was performed by using a Tali Image-based cytometer and TaliPCApp (version 1.0).

Cells were sorted into living cells (annexin V-negative/PI-negative), early apoptotic cells (annexin V-positive/PI-negative), and late apoptotic cells or necrotic cells (annexin V-positive/PI-positive), and total apoptotic cells was expressed as a percentage of annexin V-positive/PI-negative or positive cells.

Figure 8A:
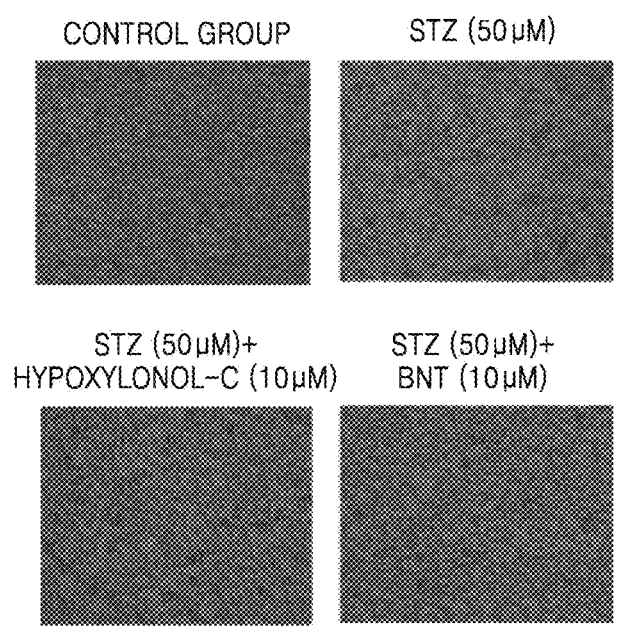
FIG. 8A is a microscopic image showing effects of streptozotocin and hypoxylonol-C or BNT on cell morphology and apoptosis in INS-1 cells and FIG. 8B is a graph showing effects of streptozotocin and hypoxylonol-C or BNT on cell morphology and apoptosis in INS-1 cells.
Figure 8B:
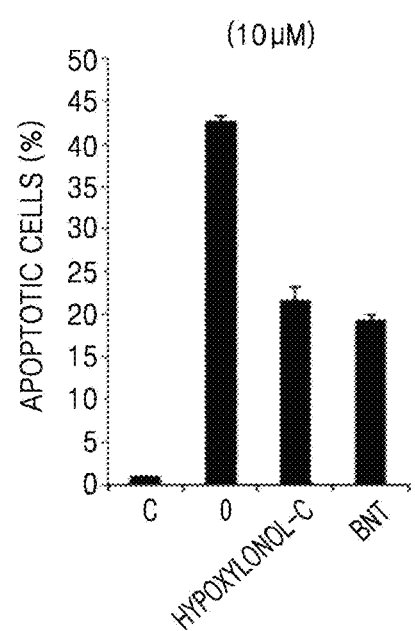

FIG. 8A is a microscopic image showing the effects of streptozotocin and hypoxylonol-C or BNT on cell morphology and apoptosis in INS-1 cells and FIG. 8B is a graph showing the effects of streptozotocin and hypoxylonol-C or BNT on cell morphology and apoptosis in INS-1 cells. In FIG. 8B, C represents a negative control group. As shown in FIG. 8A, the control group showed that most cells had rounded normal nuclei and intact plasma membranes with blue fluorescence. When 50 µM of streptozotocin was treated, chromatin condensation, nucleus condensation, and damaged plasma membrane were stained with PI to show green fluorescence, that is, apoptotic cells began to be observed. However, when 10 µM or more of hypoxylonol-C and BNT were treated, green fluorescent cells, i.e., apoptotic cells were decreased. As shown in FIG. 8B, hypoxylonol-C or BNT remarkably reduced apoptosis by streptozotocin in INS-1 cells. Table 4 shows a percentage of apoptosis of FIG. 8B.

TABLE 4

| Section | Concentration (µM) | Apoptosis (%) |
| --- | --- | --- |
| Negative control | 0 | 42.6 ± 0.5 |
| Hypoxylonol-C | 10 | 21.6 ± 1.5 |
| BNT | 10 | 19.3 ± 0.5 |

As described above, the *Hypoxylon truncatum* extract and the ingredients isolated therefrom, in particular, hypoxylonol-C, F and BNT showed no toxicity and their insulin secretion-stimulating effects were similar to or higher than that of gliclazide, and therefore, they may be used as a safe natural therapeutic agent for diabetes, which may replace the known synthetic anti-diabetic agents.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A method of stimulating insulin secretion from cells, the method comprising contacting a composition or an extract with cells, wherein the composition comprises any stereoisomer selected from the group consisting of Formulae I, II, and III, a solvate or hydrate thereof, or a mixture thereof, or a physiologically acceptable salt thereof:

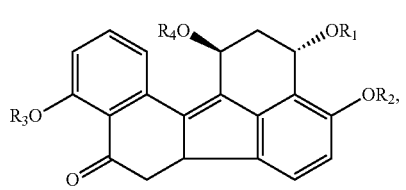

[Formula I]

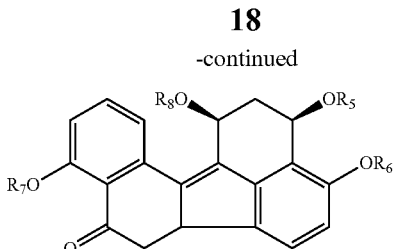

[Formula II]

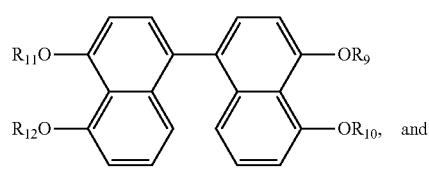

[Formula III]

wherein, in Formula I, II, and III, $R_1$, $R_2$, $R_3$, $R_4$, $R_5$, $R_6$, $R_7$, $R_8$, $R_9$, $R_{10}$, $R_{11}$, and $R_{12}$ are each independently H or $(C_1$-$C_6)$-alkyl, and the extract is a *Hypoxylon* sp. *mushroom* extract comprising any stereoisomer selected from the group consisting of Formulae I, II, and III, a solvate or hydrate thereof, or a mixture thereof, or a physiologically acceptable salt thereof:

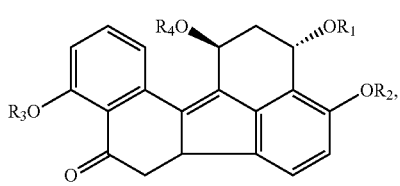

[Formula I]

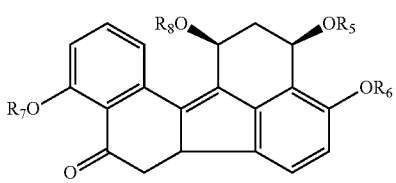

[Formula II]

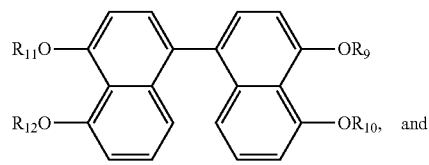

[Formula III]

wherein, in Formula I, II, and III, $R_1$, $R_2$, $R_3$, $R_4$, $R_5$, $R_6$, $R_7$, $R_8$, $R_9$, $R_{10}$, $R_{11}$, and $R_{12}$ are each independently H or $(C_1$-$C_6)$ alkyl.

2. The method of claim 1, wherein the contacting is to administer the composition or the extract to a subject.

3. The method of claim 1, wherein the cells are pancreatic beta cells.

4. The method of claim 1, wherein the method is to prevent or treat diabetes in the subject.

5. The method of claim 1, wherein $R_1$ and $R_5$ are each independently H or $(C_1$-$C_6)$-alkyl, and $R_2$, $R_3$, $R_4$, $R_6$, $R_7$, $R_8$, $R_9$, $R_{10}$, $R_{11}$, and $R_{12}$ are each independently H.

6. The method of claim 5, wherein $R_1$ and $R_5$ are each independently H, methyl, or ethyl.

7. The method of claim 1, wherein the compounds of Formula I, II, and III exist at a weight ratio of 1.0: 0.20 to 0.60: 0.50 to 1.00 in the composition.

8. The method of claim 1, the composition further comprising an excipient or a carrier which is acceptable for use in pharmaceuticals or foods.

9. The method of claim 5, wherein the composition is a pharmaceutical composition or a food composition.

10. The method of claim 4, wherein the diabetes is type 1 or type 2 diabetes.

11. The method of claim 1, the composition comprising a *Hypoxylon* sp. *mushroom* extract comprising any stereoisomer selected from the group consisting of Formulae I, II, and III, or a mixture thereof, or a physiologically acceptable salt thereof.

12. The method of claim 11, wherein the extract is extracted by an extraction method comprising contacting *Hypoxylon* sp. *mushroom* with water, $(C_1-C_3)$-alcohol, or a mixture thereof.

13. The method of claim 12, wherein the extract is obtained by fractionating the extract with a $R_{13}$—COO—$R_{14}$ solvent, wherein $R_{13}$ and $R_{14}$ are each independently $(C_1-C_6)$-alkyl.

14. The method of claim 12, wherein the extract is a fraction obtained by fractionating the extract with a $(C_4-C_{12})$-alkane solvent to obtain a fraction, removing this fraction to obtain a residue, fractionating the residue with a $R_{13}$—COO—$R_{14}$ solvent, wherein $R_{13}$ and $R_{14}$ is each independently $(C_1-C_6)$-alkyl, thereby obtained the fraction.

\* \* \* \* \*